(12) United States Patent
Jeevannavar

(10) Patent No.: US 12,653,488 B2
(45) Date of Patent: Jun. 16, 2026

(54) ELECTRONIC STETHOSCOPE

(71) Applicant: Ai Health Highway India Private Limited, Bangalore (IN)

(72) Inventor: Satish Somayya Jeevannavar, Bangalore (IN)

(73) Assignee: Ai Health Highway India Private Limited, Bangalore (IN)

( * ) Notice: Subject to any disclaimer, the term of this patent is extended or adjusted under 35 U.S.C. 154(b) by 952 days.

(21) Appl. No.: 17/074,749

(22) Filed: Oct. 20, 2020

(65) Prior Publication Data

US 2021/0030390 A1 Feb. 4, 2021

Related U.S. Application Data

(63) Continuation of application No. PCT/IB2019/000320, filed on Apr. 18, 2019.

(60) Provisional application No. 62/660,350, filed on Apr. 20, 2018.

(51) Int. Cl.
*A61B 7/04* (2006.01)
*A61B 5/00* (2006.01)
*A61B 5/316* (2021.01)
*A61B 5/339* (2021.01)

(52) U.S. Cl.
CPC ............ *A61B 7/045* (2013.01); *A61B 5/0006* (2013.01); *A61B 5/002* (2013.01); *A61B 5/316* (2021.01); *A61B 5/339* (2021.01); *A61B 5/6823* (2013.01); *A61B 5/7203* (2013.01); *A61B 5/7267* (2013.01); *A61B 5/7275* (2013.01); *A61B 5/7405* (2013.01)

(58) Field of Classification Search
CPC ....... A61B 7/045; A61B 5/0006; A61B 5/002; A61B 5/316; A61B 5/339; A61B 5/6823; A61B 5/7203; A61B 5/7267; A61B 5/7275; A61B 5/7405; A61B 7/04
See application file for complete search history.

(56) References Cited

U.S. PATENT DOCUMENTS

2006/0169529 A1* 8/2006 Tamakoshi ............... A61B 7/04
181/131
2011/0087135 A1* 4/2011 Ferzli ................... A61B 5/0035
706/54

(Continued)

FOREIGN PATENT DOCUMENTS

WO WO 2016/206704 A1 12/2016
WO WO 2017/120138 A1 7/2017

OTHER PUBLICATIONS

International Search Report and Written Opinion for corresponding PCT Application No. PCT/IB2019/000320, dated Sep. 24, 2019, 11 pages.

(Continued)

*Primary Examiner* — Justin Xu
(74) *Attorney, Agent, or Firm* — Dority & Manning, P.A.

(57) ABSTRACT

The present invention relates to a stethoscope configured to mechanically capture chest sounds, convert those sounds into electronic wave forms, visualize the signal and analyze the wave forms using digital signal processing techniques, and use the results of the analysis to predict using artificial intelligence and machine learning based models to provide a differential diagnosis based on the chest sounds to a high degree of accuracy.

4 Claims, 7 Drawing Sheets

(56) References Cited

U.S. PATENT DOCUMENTS

| | | | | |
|---|---|---|---|---|
| 2011/0137209 | A1* | 6/2011 | Lahiji | H04R 1/406 |
| | | | | 600/586 |
| 2013/0085364 | A1* | 4/2013 | Lu | G16H 40/67 |
| | | | | 600/523 |
| 2015/0045641 | A1* | 2/2015 | Rule | A61B 5/150229 |
| | | | | 600/347 |
| 2015/0238148 | A1* | 8/2015 | Georgescu | G06F 18/28 |
| | | | | 600/408 |
| 2016/0100817 | A1* | 4/2016 | Hussain | A61B 7/04 |
| | | | | 600/528 |
| 2016/0192846 | A1* | 7/2016 | Shekhar | A61B 7/02 |
| | | | | 600/528 |
| 2016/0287207 | A1 | 10/2016 | Xue | |
| 2016/0354054 | A1 | 12/2016 | Minegishi et al. | |
| 2017/0007187 | A1* | 1/2017 | Breneisen | G16H 40/63 |
| 2017/0235935 | A1* | 8/2017 | Song | G06F 21/35 |
| | | | | 726/19 |
| 2018/0049716 | A1 | 2/2018 | Rajagopal et al. | |
| 2018/0277245 | A1* | 9/2018 | Boesen | H04R 1/1016 |
| 2019/0038148 | A1* | 2/2019 | Valys | A61B 5/02405 |
| 2019/0083056 | A1* | 3/2019 | Abiri | A61B 7/04 |
| 2019/0160287 | A1* | 5/2019 | Harrer | G16H 10/60 |
| 2019/0216420 | A1* | 7/2019 | Hsu | A61B 7/02 |
| 2021/0076977 | A1* | 3/2021 | Abeyratne | A61B 5/7267 |

OTHER PUBLICATIONS

EPO Communication for corresponding EP Application No. 19737581.9, dated Apr. 11, 2023, 8 pages.

* cited by examiner

AI/ML Stethoscope

Ⓐ  Chestpiece (Input)

diaphragm

24

Artificial Intelligence
+ Machine learning chip
with processor bell

Ⓑ  process
Microphone + wireless + amplifier diaphragm       25          Micro-electro-mechanical
                                              microphone

7'

Sound
waves

AI/ML
chip with
processor

8

13

25'    26    27    28    28'

Stethoscope housing

Ⓒ

ELECTRONIC STETHOSCOPE

CROSS-REFERENCE TO RELATED APPLICATIONS

The present application is a continuation application of PCT international application serial no. PCT/IB2019/000320, filed on 18 Apr. 2019, which claims priority from U.S. application Ser. No. 62/660,350, filed on 20 Apr. 2018, all herein incorporated by reference in their entireties.

TECHNICAL FIELD OF INVENTION

The present invention relates generally to the field of electronic stethoscopes and more specifically to electronic stethoscopes configured to provide differential diagnoses.

BACKGROUND OF THE INVENTION

Heart and Lung Disorders (more formally, cardio vascular, respiratory & related disorders, or "CVRDs") represent the leading cause of death worldwide i.e. 55.9 million deaths globally in 2012. Cardiovascular deaths (CVD) accounted for an estimated 31% of all global deaths (An estimated 17.7 million people died from CVD in 2015). Of these deaths, an estimated 7.4 million were due to coronary heart disease and 6.7 million were due to stroke, followed by respiratory deaths (4.0 million). Over three quarters of CVRDs deaths take place in low- and middle-income countries. Most CVRDs can be prevented by addressing behavioral risk factors such as tobacco use, unhealthy diet and obesity, physical inactivity, and harmful use of alcohol. Critical to prevention is early detection and cost-effective management.

The stethoscope is the most basic tool used to initially detect CVRDs and is the first point of clinical examination for heart and lung sounds. The stethoscope was invented in 1816 by Rene Laennec. Today's stethoscope remains largely unchanged from the original, being a mechanical device used to amplify chest sounds (namely heart, lung, bowel and other bodily sounds) so that a medical practitioner (doctor, nurse, physician's assistant, EMT, etc.) can hear the sounds and arrive at a diagnosis based on experience and familiarity with "normal" and "abnormal" chest sounds. However, there is a lot of subjectivity in the interpretation of chest sounds. On average a medical practitioner needs 2-5 years of training and experience before he or she can successfully identify clinically significant normal and abnormal chest sounds and make a proper differential diagnosis.

It thus is shown that there is a need for an improved stethoscope that can automatically detect chest sounds, analyze them, and display a resulting differential diagnosis, greatly assisting medical practitioners in early detection of CVRDs. Heart and Lung Disorders (more formally, cardio vascular, respiratory and related disorders, or "CVRDs") represent the leading cause of death worldwide i.e. 55.9 million deaths globally in 2012. Cardiovascular deaths (CVD) accounted for an estimated 31% of all global deaths (An estimated 17.7 million people died from CVD in 2015). Of these deaths, an estimated 7.4 million were due to coronary heart disease and 6.7 million were due to stroke, followed by respiratory deaths (4.0 million). Over three quarters of CVRDs deaths take place in low- and middle-income countries. Most CVRDs can be prevented by addressing behavioral risk factors such as tobacco use, unhealthy diet and obesity, physical inactivity, and harmful use of alcohol. Critical to prevention is early detection and cost-effective management.

The stethoscope is the most basic tool used to initially detect CVRDs and is the first point of clinical examination for heart and lung sounds. The stethoscope was invented in 1816 by Rene Laennec. Today's stethoscope remains largely unchanged from the original, being a mechanical device used to amplify chest sounds (namely heart, lung, bowel and other bodily sounds) so that a medical practitioner (doctor, nurse, physician's assistant, EMT, etc.) can hear the sounds and arrive at a diagnosis based on experience and familiarity with "normal" and "abnormal" chest sounds. However, there is a lot of subjectivity in the interpretation of chest sounds. On average a medical practitioner needs 2-5 years of training and experience before he or she can successfully identify clinically significant normal and abnormal chest sounds and make a proper differential diagnosis.

It thus is shown that there is a need for an improved stethoscope that can automatically detect chest sounds, analyze them, and display a resulting differential diagnosis, greatly assisting medical practitioners in early detection of CVRDs.

SUMMARY OF THE INVENTION

The present invention is an electronic stethoscope that records and visualizes chest sounds and furthermore employs artificial intelligence and machine learning (AI/ML) models to analyze chest sounds and provide a differential diagnosis. Comparative data may be remotely stored, with the stethoscope of the present invention incorporating a communication means for accessing such data. Over time, predictive analytics will lead to better mapping with existing clinically validated chest sounds and improved diagnosis. The result is that the present invention will bring down the learning curve, especially for the nurse, physician assistant, and newly minted medical student. It will enable better efficiency in screening and primary/preventive care, thereby reducing the burden on already overcrowded secondary and tertiary healthcare providers.

The stethoscope of the present invention, in one embodiment, comprises a sound capture component, a sound processing component, a communications component, a sound analyzing component, and an output data display component. The sound capture component may combine both mechanical and electronic elements, such as a traditional diaphragm and bell to capture sound waves, augmented by a microphone or microphone array, an amplifier, adaptive noise cancellation and beamforming technology. The sound processing component comprises a digital signal processing filter and an artificial intelligence/machine learning chip set which takes the sound waves captured by the sound capture component and converts them into wave forms that can be compared against standard data sets. The communications component may comprise wireless or DECT (Digital Enhanced Cordless Telecommunications) or BLUETOOTH (Bluetooth SIG, Inc.) technology to connect to a remote store of standardized data. The differential diagnosis of the sample data is performed using machine learning and artificial intelligence models developed using standardized dataset remotely or by the resident chip set of the sound processing component. The wave forms and the relevant time/frequency and time-frequency parameters may be displayed on the output data display component, providing a visual reference, and a textual indication of up to three diagnosis may also be displayed in the form of 2D, 3D augmented, virtual or mixed reality. It is a well-known fact that about 35% of the general population are acoustic learners, 60% visual learners and a very small minority learn through Kinesthetic or Touch methodology. By combining the visualization component to the output display unit, the physician will benefit immensely with the combined Acoustic+Visual output as he is already well adapted to identifying the acoustic characteristics of the Heart, Lung or other body sounds.

The need for an improved stethoscope is according to the present invention solved by the provision of a stethoscope configured to mechanically capture chest sounds, where the stethoscope comprises:

a sound capture component, a sound processing component, a communications component, and an output data display component;

wherein the sound capture component is configured to mechanically capture sound waves produced within an upper torso region of a human subject, the sound processing component is configured to convert the sound waves captured by the sound capture component into electronic wave forms, to analyze the electronic wave forms using digital signal processing techniques and use these parameters against artificial intelligence and machine learning models built on standardized data.

the communications component is configured to transfer the waveform to a remote repository to be saved or to communicate with a remote repository for the AWL build using standardized data that corresponds to differential diagnosis of diseases and medical conditions that produce distinctive sound waves within an upper torso region of a human subject, and the data display component is configured to display a differential diagnosis based on the prediction of the sound waves against the deployed AI/ML models and accessed by communications component.

According to an embodiment of the invention the sound capture component comprises a bell fitted with a diaphragm, microphone such as MEMS, measurement etc. and an electronic amplifier in connection with the microphone.

According to an embodiment of the invention the sound capture component further comprises adaptive noise cancellation and or ambient noise reduction technology used to screen out unwanted sound waves.

According to an embodiment of the invention the sound capture component further comprises a removable memory chip suitably configured to have the captured sound waves recorded thereon.

According to an embodiment of the invention the sound processing component comprises a digital signal processing filter, and an artificial intelligence/machine learning chip.

According to an embodiment of the invention the sound processing component further comprises a removable memory chip suitably configured to have the electronic wave forms recorded thereon.

According to an embodiment of the invention the communications component uses wireless technology such as BLUETOOTH (Bluetooth SIG, Inc.), Wi-Fi or DECT (Digital Enhanced Cordless Telecommunications) etc.

According to an embodiment of the invention the display component is a connected device such as smart phone, laptop etc.

According to an embodiment of the invention differential diagnosis at the output of the sound processing component can be integrated with other parameters from an electronic medical record database to make an improved holistic differential diagnosis.

According to an embodiment of the invention the sound capture component can start automatically recording chest sounds from the person's torso when the chest piece is in contact with the person's body.

According to an embodiment of the invention the sound capture component can localize the position of the chest piece on the person's torso.

According to an embodiment of the invention the sound capture component have an extra microphone to record a user's voice with optional voice-to-text technology, thus enabling the stethoscope to act as a dictation machine to assist with electronic medical recordkeeping (EMR).

According to an embodiment of the invention the processed output data can be displayed in the form of an augmented, virtual or mixed reality application, thus enabling the stethoscope to help in patient education or train fresh medical and nursing graduates.

According to an embodiment of the invention the device can house a SIM (Subscriber Identification Module) card and payment gateway interface for seamless transfer of data in a secure, encrypted format to protect patient confidentiality and close the loop with payment between end-user and any stakeholder.

According to an embodiment of the invention the chest piece is provided with an array of vibrational transducers configured to pick up vibrations from a patient's body.

According to an embodiment of the invention the chest piece is provided with an array of acoustic transducers, such as microphones, configured to pick up sounds from a patient's body.

According to an embodiment of the invention the vibration transducers and the acoustic transducers are provided as a plurality of separate combined transducers, each comprising an individual vibration and acoustic transducer.

According to an embodiment of the invention the array of transducers is a 3-dimensional array.

According to an embodiment of the invention the stethoscope comprises different functional units of the stethoscope, such as an INPUT UNIT, a PROCESSING UNIT, an OUTPUT UNIT and an application/user interface device, where some or all of the different functional units are geographically distributed, such that some of the units are local units, i.e. units that can be used in the vicinity of a patient, while other functional units are external, such as provided in cloud servers or other remote facilities.

According to an embodiment of the invention, a stethoscope according to any of the preceding claims, where the stethoscope further comprises additional features comprising one or more of the following:

Wireless charging 60 of the electronic components in the stethoscope.

Touch based sensors 61 provided on the chest piece with auto-record facility.

Array-based sensors 62.

GPS facilities 63 and localization technologies for localizing the position on the torso of a patient as shown at 71.

AI/ML chipset 64 in the chest piece.

SIM Card 65 in the chest piece.

A scan to pay facility/payment gateway interface, 73 72.

Augmented, virtual or mixed realty facilities as schematically illustrated at 75

The clinical utility of the invention is made possible by innovation structured into three broad units and processes:

1. Input Unit

Data capture or acquisition of the sound waves and the integrated electronic component which converts the sound waves into electrical signal and transmits it to the processing unit.

2. Processing Unit

Assessment of the signal/sound wave quality and filtering of the artifacts/normalization of the clinically relevant heart, lung or bowel sounds and segmentation and classification of the sound and/or visual wave patterns into clinically established and documented known physiological (normal) or pathological (abnormal) phases or patterns. The entire processing activities may be carried out in an embedded chipset which consists of components within or outside of the device connected via wireless connectivity such as Wi-Fi, BLUETOOTH (Bluetooth SIG, Inc.) etc. to a cloud server housing the data warehouse which consists of data repositories synchronized on an ongoing basis.

3. Output Unit

The output unit may be developed as a continuous feedback loop mechanism comprising the input and processing unit datapoints (soundwaves, visual wave formats, features and) following layers of human and machine learning analysis and classification algorithm (not just limited to these below categories):

a. Artificial Neural Network (ANN) based classification to support clinical diagnostic decision making using some of the input signal features such as wavelet features and patterns, time, frequency, and complexity-based features and time-frequency features. Additional features and combination of established approaches such as discrete wavelet transform, fuzzy logic, fast Fourier transform (FFT) are being explored to differentiate and classify normal, abnormal and specific clinical condition-based patterns.

b. Support Vector Machine (SVM) based classification which is a form of supervised machine learning used to classify normal and abnormal heart sounds based on wavelet features and frequency band ranges.

c. Combination of Supervised Learning and Hidden Markov Model (HMM) which analyses the heart sounds S1 and S2, the time interval duration between systole and diastole frequency features and patterns combined with logistic regression and Gaussian distribution-based probabilities.

d. Unsupervised Clustering based classification using k-nearest neighbors (kNN) which classifies heart sounds as normal and abnormal based on analyses of S1 and S2 time and frequency features extraction by linear decomposition and tiling partition of the time-frequency plane.

e. Deep learning model using CNN on the 2D time-frequency graphs of the data samples or RNN/LTSM based models for the time-domain signal.

Application

All of the above processed output Data (Acoustics, Visual, 2D, 3D, Augmented, Virtual Reality and Mixed Reality) may be made available using BLUETOOTH (Bluetooth SIG, Inc.), Wi-Fi, Direct Wireless connection to an internet connected device, Smart Phone, Streaming Device, SIM Card, Direct wireless connection to the Internet, or it may be a connection to the Payment Gateway Interface

BRIEF DESCRIPTION OF DRAWINGS

The present invention will be more readily understood by reference to the following detailed description of non-limiting embodiments of the invention taken in conjunction with the figures, where.

DETAILED DESCRIPTION OF THE INVENTION

In the following detailed description of the invention different embodiments of the invention are described, but it is emphasized that these embodiments are only non-limiting examples of how the basic ideas of the invention can be carried out in practice.

Figure 1:
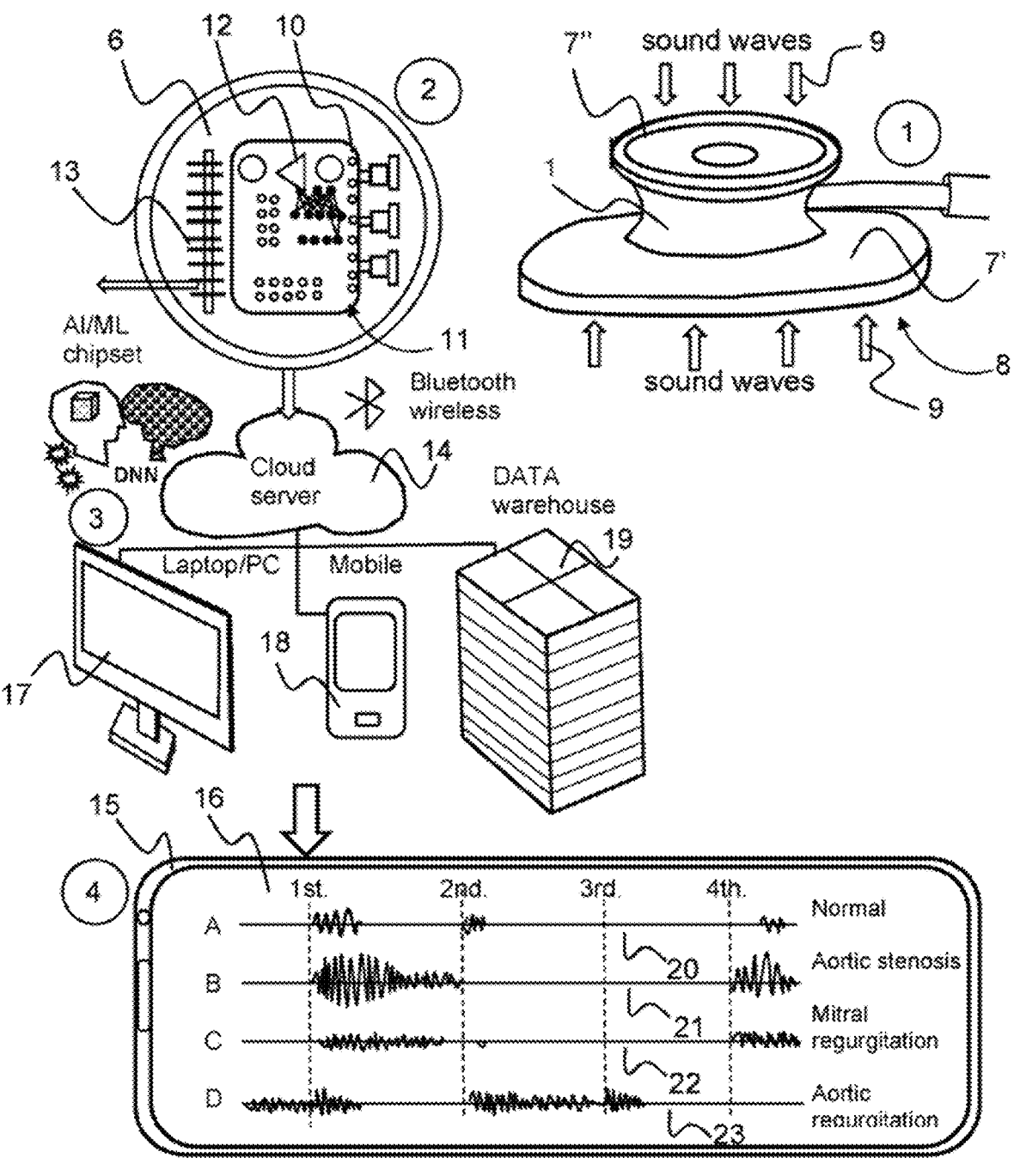
FIG. 1 shows a schematic depiction of one embodiment of the present invention having a sound capture component, a sound processing component, a communications component, and an output data display component.

With reference to FIG. 1 there is shown a schematic depiction of one embodiment of the present invention having a sound capture component generally designated by reference numeral 1, a sound processing component generally designated by reference numeral 2, a communications component generally designated by reference numeral 3, and an output data display component generally designated by reference numeral 4.

The stethoscope of the present invention comprises a housing 5. The housing has an interior cavity 6 in which mechanical or electronic components are stored. Attached to one end of the housing is a conical portion comprising 7' a cavity covered by a diaphragm 8 (not visible in FIG. 1). Axially opposite to the conical portion 7' there is provided the bell 7". Sound waves 9 can enter the stethoscope through either of these portions, i.e. through the conical portion with the diaphragm and/or through the bell. This is a typical configuration found in traditional stethoscopes. Either the bell conical portion 7' or the bell 7" of the housing 1 is placed against the patient's torso, and sound waves 9 emanating from the patient's thoracic region are concentrated by either of these portions in a manner well known within the art, whereby the sound waves are amplified. In the stethoscope of the present invention, there is a microphone 10 (such as MEMS, (micro-electromechanical systems)) or microphone array 11 in connection with an electronic amplifier 12, both located within the housing 1. The microphone 10 or the microphone array 11 captures the sound waves amplified by the diaphragm 8 and the electronic amplifier 12 further amplifies the sound waves captured by the microphone 10 or microphone array 11. In one embodiment adaptive noise cancellation and/or beamforming technology may be used to screen out unwanted sound waves, such as those generated by the bell 7 and/or diaphragm 8 moving across skin, hair, or clothing, or ambient sounds.

The electronically enhanced sound waves are then processed by a digital signal processing filter and an artificial intelligence/machine learning chip 13 set located within the housing 1. This converts the sound waves into a digital signal that can be processed electronically as well as displayed visually. Once processed, the digital wave forms are ready for being used against the artificial intelligence/machine learning models developed using standardized wave forms which have been clinically correlated to different disease states. These digital wave forms may be stored locally in memory for later retrieval and playback. They can also be used later for training and improving the artificial intelligence/machine learning models.

In one embodiment, the artificial intelligence/machine learning models are deployed remotely from the stethoscope of the present invention. The stethoscope thus uses its communications component 3 to access those models remotely on the cloud server 14 or housed locally on the device. The communications component 3 may be any wireless connection (such as Wi-Fi, blue tooth or DECT (Digital Enhanced Cordless Telecommunications) to a connected device, such as a smart phone, or it may be a direct wireless connection to the "cloud". The communications component may be used to send the enhanced digital wave forms to a remote site or local processing unit for prediction using the AI/ML models built using standardized wave forms, and then to retrieve the results back, or the AWL models may be deployed the AWL chipset 13 on the stethoscope for local analysis and prediction. Alternatively, the local device to which the communications component connects, such as a smart phone, can perform the analysis and prediction using a locally deployed AI/ML, model or one deployed remotely on the cloud server 14, and then communicate the results to the stethoscope for display via the communications component, or simply display the results itself.

Thus, according to one embodiment, raw data is gathered by the stethoscope, is processed by the stethoscope to enhance the data and prepare it for prediction, and then is sent to a remote site for comparison, analysis, detection and/or prediction against AI/ML models built using standardized wave forms for analysis, with the results communicated back to the stethoscope for display. In this embodiment the stethoscope is primarily a data capture device. In another embodiment, raw data is gathered by the stethoscope, is processed by the stethoscope to enhance the data and prepare it for comparison, analysis, detection and/or prediction, the analysis and prediction is performed locally or remotely in the cloud server by the AI/ML chipset on the stethoscope, and the results are displayed by the stethoscope. In this embodiment the stethoscope both captures data and also performs all of the analysis. In yet another embodiment raw data is gathered by the stethoscope, is processed by the stethoscope to enhance the data and prepare it for prediction, is sent wirelessly to a local processing device such as a smart phone, the AWL models built using standardized wave forms are retrieved by the smart phone from a remote location using wireless technology, the analysis and prediction is made by an app on the smart phone, and the results are displayed by the smart phone. This is a hybrid embodiment with analysis being conducted locally but leveraging an independent device, thus simplifying the design of the stethoscope itself. Other embodiments mixing and matching these components are also contemplated.

The stethoscope may contain a display screen integrated with the housing, or it may rely upon the display screen 16 of a local, wirelessly connected device 15 such as a laptop or smart phone, or in the form of augmented, virtual or mixed reality application. The display screen 16 may show a visual representation of the chest sounds and some of the features extracted from the waveform alongside in the form of augmented, virtual or mixed reality application. It may also offer an audio component whereby the user can listen to the chest sound, as enhanced by the sound processing component and recorded by the stethoscope. The audio may be controlled by a volume control feature. The above formats of output display unit in the form of Acoustics, Visualization in the form of augmented, virtual or mixed reality application will help the end user (patient, doctor or any user) for patient education to know more about the clinical condition which helps in adherence and compliance of specific therapy or medication. Finally, up to three differential diagnoses may be textually displayed on the display component.

Artificial intelligence and machine learning algorithms are used in the prediction phase, whereby the captured data is tested against an AWL model built using standardized data. Differences in the data are accounted for by the artificial intelligence algorithms to find a "best match" as well as one or more alternative matches. In addition, machine learning technology is incorporated to dynamically improve the artificial intelligence algorithms so that over time the comparison feature will become more and more accurate. Some or all of this can be handled remotely, for example, using IBM's Watson technology.

Figure 2:
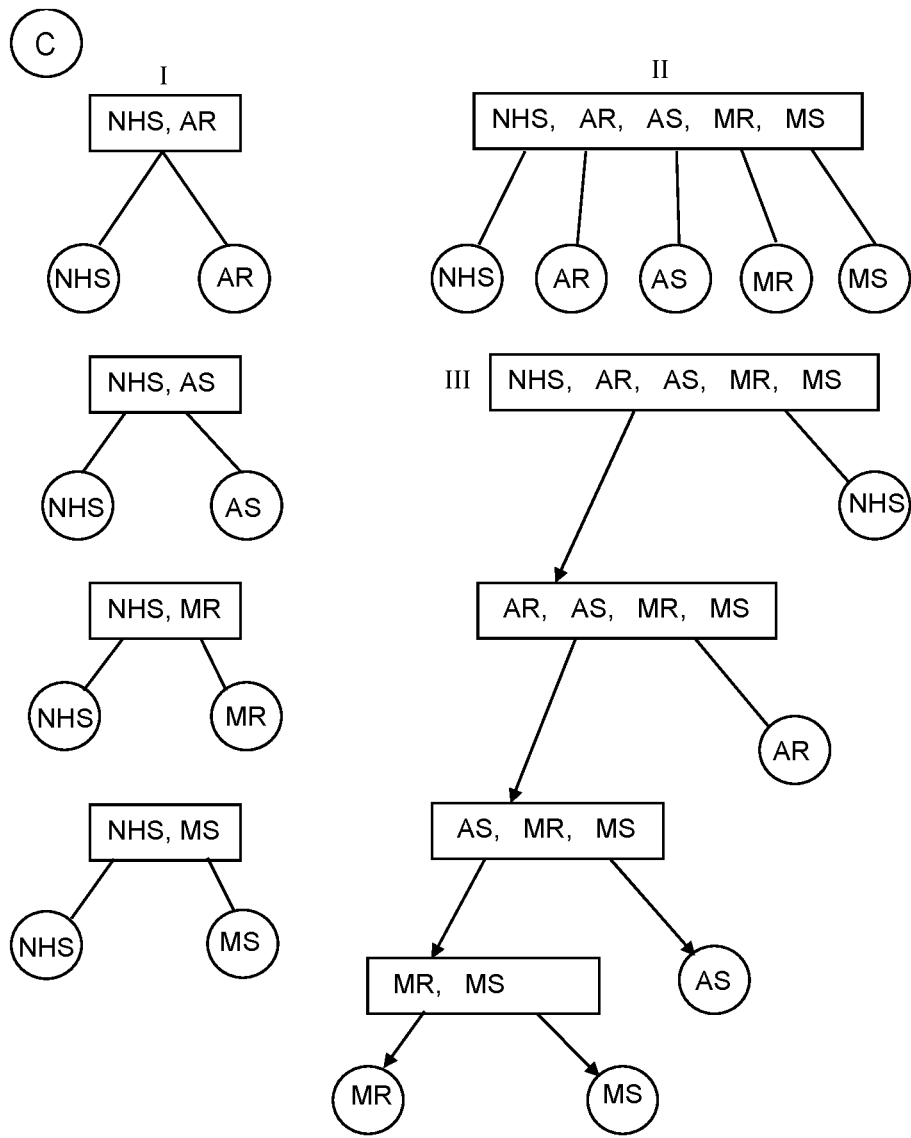
FIG. 2 shows a series of flow charts depicting different possible differential diagnoses based on the type of input.

With reference to FIG. 2 there is shown a series of flow charts depicting different possible differential diagnosis based on the type of input. In FIG. 2, the following abbreviations are used:

NHS—Normal Heart Sound
AR—Aortic Regurgitation
AS—Aortic Stenosis
MR—Mitral Regurgitation
MS—Mitral Stenosis Three types of classification are mentioned in FIG. 2 (binary independent, binary hierarchy, multiple class) which essentially reflect how an experienced doctor or other qualified person would think while diagnosing of the above heart conditions based on their acoustic/visual patterns+permutations and combinations.

According to the invention, the same or similar diagnosing is obtained using for instance (but not limited to) the machine learning analysis and classification algorithms mentioned in the description of the OUTPUT UNIT above.

Figure 3:
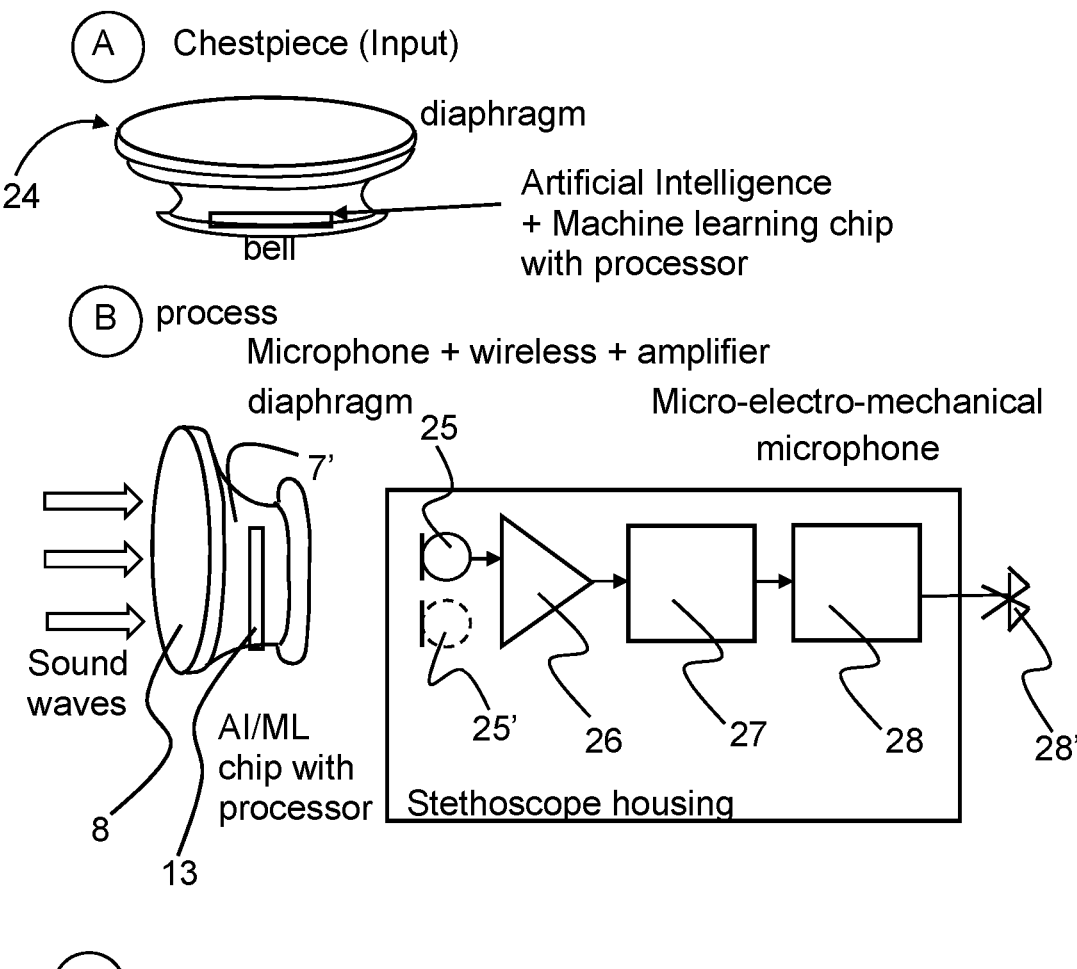
FIG. 3 shows a schematic depiction of another embodiment of the present invention having a sound capture component and a sound processing component, whereby the sound capture component comprises a diaphragm, a bell, a micro-electro-mechanical microphone, and an amplifier and where the sound processing component comprises an artificial intelligence/machine learning chip set and adaptive noise cancellation; and the communications component comprises wireless/BLUETOOTH (Bluetooth SIG, Inc.) technology.

With reference to FIG. 3 there is shown a schematic depiction of another embodiment of the present invention having a sound capture component 24 and a sound processing component, wherein the sound capture component comprises a diaphragm 9, a bell 7", a micro-electro-mechanical microphone 25, and an amplifier 26, where the sound processing component comprises an artificial intelligence/machine learning chip set 13 and adaptive noise cancellation 27. The communications component comprises wireless/BLUETOOTH (Bluetooth SIG, Inc.) technology 28 by means of which the output from the stethoscope can be wirelessly transmitted to further analysis, diagnosing models and displays and the outputted digital wave forms can be used against artificial intelligence/machine learning models developed using standardized wave forms which have been clinically correlated to different disease states. These digital wave forms may be stored locally in memory for later retrieval and playback. They can also be used later for training and improving the artificial intelligence/machine learning models.

Figure 4A:
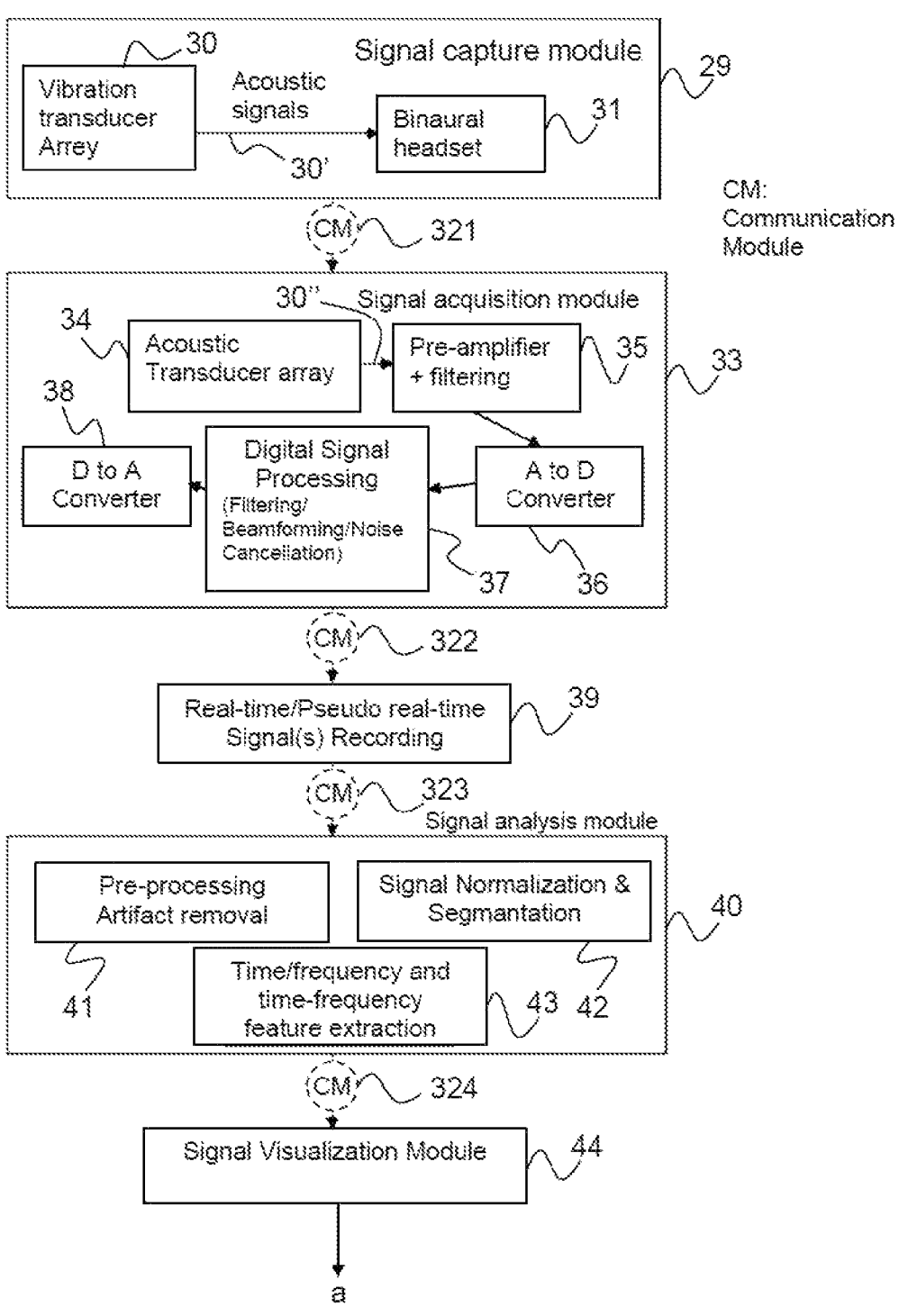
FIGS. 4a and 4b show a schematic block diagram illustrating the various functional entities of an embodiment of the invention.
Figure 4B:
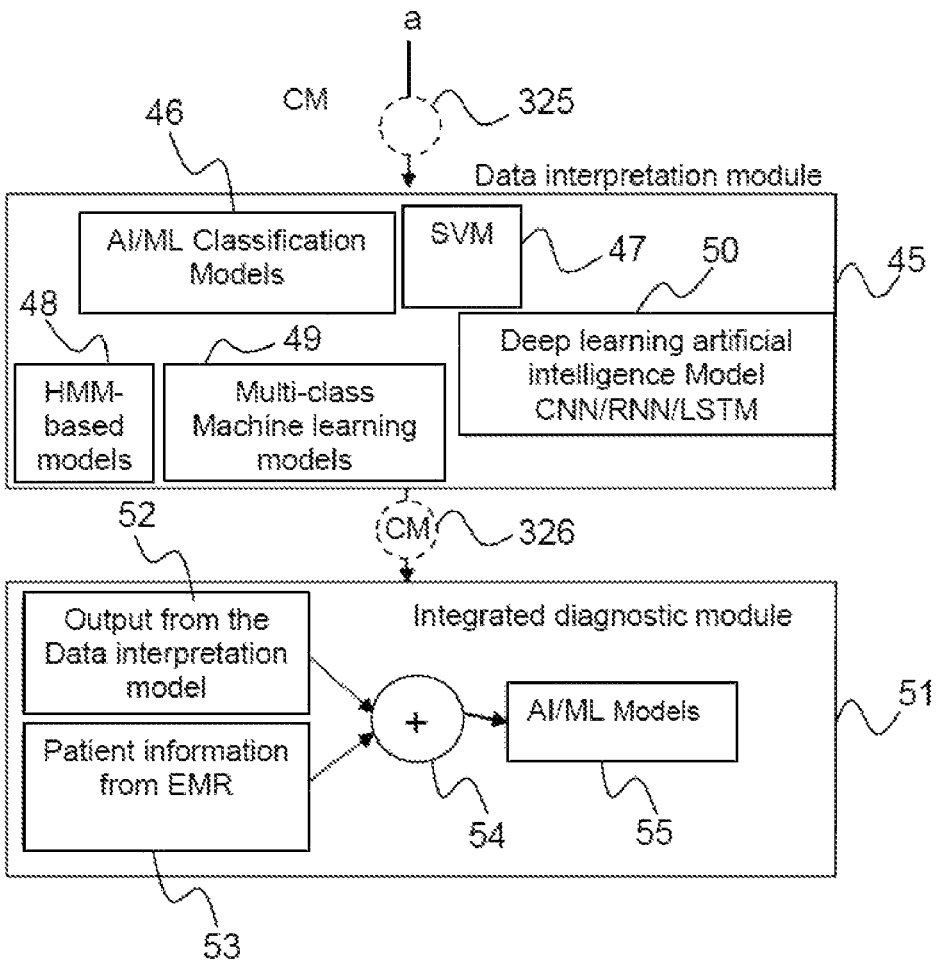

With reference to FIGS. 4a and 4b (the latter being a continuation of 4a) there is shown a schematic block diagram illustrating the various functional units or modules of an embodiment of the invention.

The signal capture module 29 of this embodiment comprises a vibration transducer array configured to pick up vibrations generated by a human body. The acoustic signals thereby generated by the vibration transducer array 30 are provided to a binaural headset 31 and to the signal acquisition module 33 via the communications module (CM) 321. The vibration transducer converts bodily vibration into acoustic signals (for instance as the diaphragm portion of a traditional Littmann stethoscope does).

The acoustic signals 30', 30" provided by the vibration transducer array 30 and the acoustic transducer (microphone) array 34, respectively, are pre-amplified and filtered in block 35 and then converted from analog to digital signals in the A/D converter 36. The digital signal from the A/D converter 36 is provided to digital processing means (DSP) 37, in which for instance further filtering, beamforming and noise cancellation can be implemented. The processed digital signal from the DSP 37 is converted to an analog signal in D/A converter 38, from which it is outputted from the signal acquisition module 33 via the CM 322.

A real-time of pseudo real-time of the signals provided by the signal acquisition module 33 is carried out in block 39.

In the signal analysis module 40 (that is accessed via the CM 323) a pre-processing and artifact removal is carried out in block 41 and signal normalization and segmentation is carried out in block 42. Time/frequency and/or time-frequency feature extraction is carried out in block 43. The signal analysis module provides signals (via CM 324) to a signal visualization module 44.

The signal from the signal visualization module 44 is passed via CM 325 to the data interpretation module 45 that comprises one or more artificial intelligence/machine learning models commonly designated by block 46. Such models comprise, but are not necessarily limited to, a support vector machine (SVM) 47, deep learning artificial intelligence model (CNN/RNN/LSTN) 50, multi-class machine learning models 49 and hidden Markov model (HMM)-based models 48. Using AI/ML classification models and comparing with AI/ML models built using standardized data it is possible to arrive at a diagnosis with a given degree of probability for instance by comparison with information from electronic medical recordkeeping (EMR). This is in the shown embodiment carried out in the integrated diagnostic module 51 as schematically depicted in FIG. 4b.

In the data interpretation module 45, AI/ML classification models are used to interpret the signals (waveforms etc.) provided from the signal visualization module 44, such that a differential diagnose based on the signals picked up by the chest piece of the stethoscope can be obtained. Such AI/ML classification models comprise (but is not necessarily limited to) a support vector machine (SVM) 47, a deep learning artificial intelligence model (CNN/RNN/LSTM) 50, multi-class machine learning models 49 and hidden Markov based (HMM) models 48.

In the integrated diagnostic module 51, output from the data interpretation module 52 together 54 with corresponding patient information from EMR 53 is used to arrive at the desired diagnosis.

In the embodiment shown in FIGS. 4(a) and 4(b) communication between modules are carried out via the communication modules (321, 322, 323, 324, 325, 326). In the block diagram, these communication modules are shown as separate modules, but in practical implementations they may be implemented by a single module. It is further possible that at least some of the modules shown in FIGS. 4(a) and 4(b) are integrated into a single module and that, consequently, wireless communication (or any communication) is hence not needed for those integrated modules.

Figure 5:
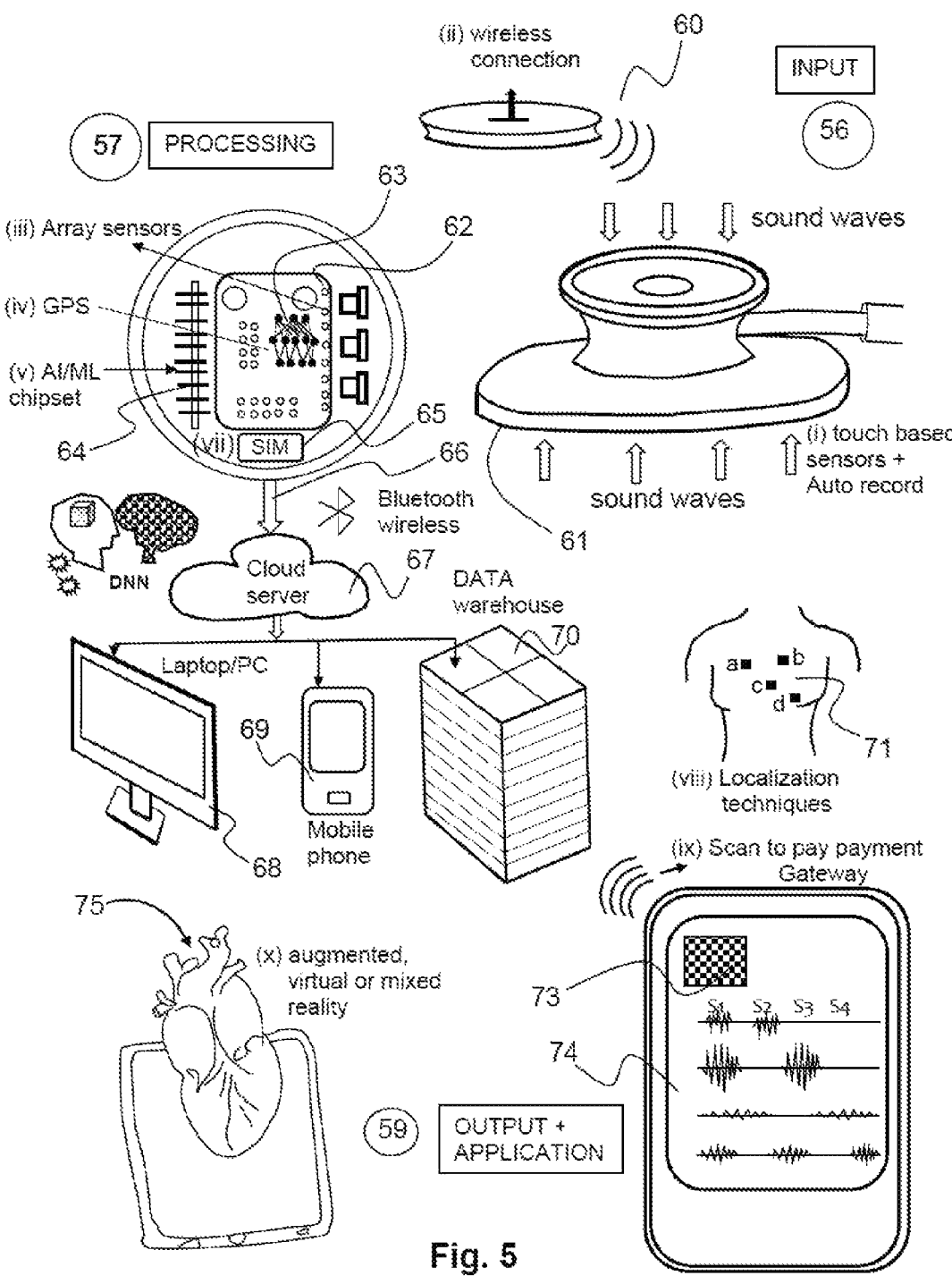
FIG. 5 shows a schematic depiction of still another embodiment of the present invention with a number of features added.

With reference to FIG. 5 there is shown a schematic depiction of still another embodiment of the present invention with a number of features added. These features comprise:

Wireless charging 60 of the electronic components in the stethoscope.

Touch based sensors 61 provided on the chest piece with auto-record facility.

Array-based sensors 62.

GPS facilities 63 and localization technologies for localizing the position on the torso of a patient as shown at 71.

AI/ML, chipset 64 in the chest piece.

SIM

Card 65 in the chest piece.

A scan to pay facility/payment gateway interface, 73 72.

Augmented, virtual or mixed realty facilities as schematically illustrated at 75

According to the invention, the various processing facilities of the electronic stethoscope may be distributed, such that for instance initial filtering and/or beamforming may be carried out by functional entities located in the chest piece whereas other processing (such at those listed under Items a, b, c, d and e above) may be provided on one or more cloud servers 67 that can be wirelessly accessed from the stethoscope chest piece as well as from output equipment/user interface means, such as computers 68, mobile phones 69, etc. The necessary data warehouse 70 may also be geographically located remote from the other functional entities of the invention. Hence, the term "electronic stethoscope" as used in the present specification including the claims is to be construed broadly and relate generally to the entire—geographically distributed—system comprising the basic functional entities that comprise the INPUT UNIT, PROCESSING UNIT, OUTPUT UNIT and APPLICATION mentioned above.

This may however not rule out that all necessary functional entities may alternatively be integrated into a single, unified physical entity that then constitutes the electronic stethoscope of the present invention.

Figure 6A:
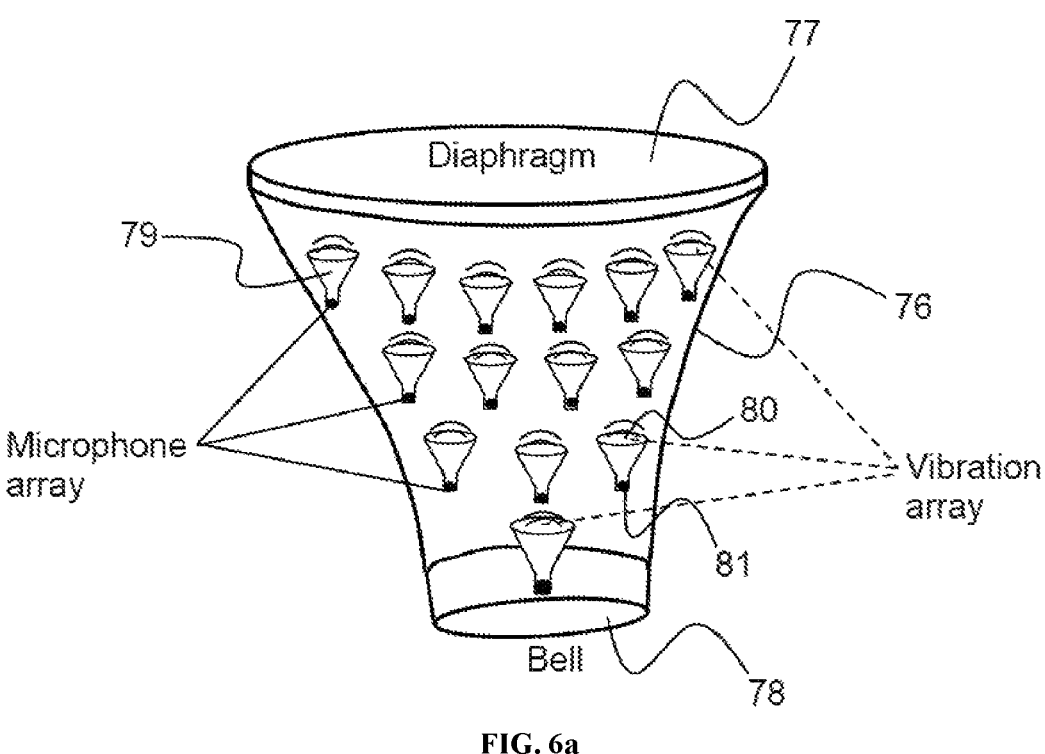
FIGS. 6a and 6b show a schematic representation of a chest piece according to an embodiment of the invention, where the chest piece is provided with a plurality of vibration transducers and acoustic transducers (microphones) forming a 3-dimensional array of transducers.
Figure 6B:
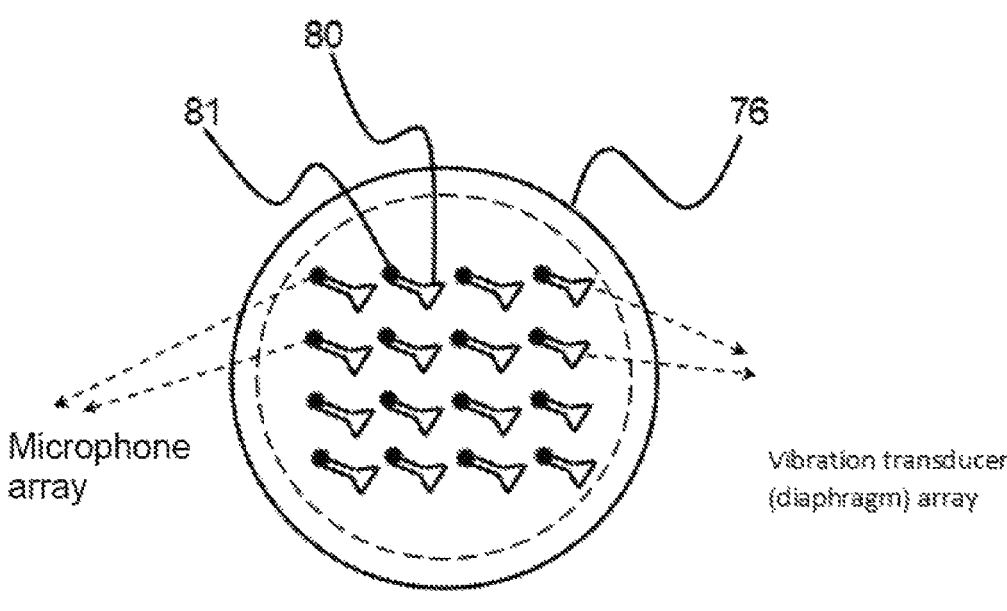

With reference FIGS. 6(a) and 6(b) there is shown a schematic representation of a chest piece 76 according to an embodiment of the invention comprising a diaphragm end portion 77 and a bell end portion 78, where the chest piece is provided with a plurality of vibration transducers and acoustic transducers (microphones) forming a 3-dimensional array of transducers. In this embodiment, each of the transducers 79 of the array comprises a vibrational transducer 80 and an acoustic transducer 81. Arrays of separate vibrational transducers and acoustic transducers would how-ever also be possible without departing from the scope of the present invention.

Other embodiments of the present invention may include certain convenience features, such as using the microphone to record a medical practitioner's voice, with optional voice-to-text technology, thus enabling the stethoscope to act as a dictation machine to assist with electronic medical record-keeping (EMR). In some embodiments, the stethoscope will comprise a removable memory chip, to hold stored digital wave forms; this would allow transfer of the patient's data by use of the memory chip when wireless communications are not available.

In all embodiments, the stethoscope will have a power supply. Preferably, the power supply will be a rechargeable battery located within the housing of the stethoscope. In some embodiments, there will be a provision to wirelessly charge the rechargeable battery in the housing.

Other embodiments of the present invention may include convenience features such as automatic sound capturing as soon as the diaphragm and/or bell is touching the person's chest region using either touch-based technology or signal processing software to trigger the start and stop of data capture or a hybrid of both. In some embodiments, the exact location of the chest piece diaphragm or bell on the person's torso will be captured using localization technologies such as ultrasound, GPS, accelerometers and/or BLUETOOTH (Bluetooth SIG, Inc.) technology. This will be used to guide the user of the stethoscope to the exact location of the body to pick the accurate sounds. The embodiments may house storage device, SIM card to process the final output data locally or remotely and connect to a Payment Gateway Interface to complete a financial transaction. The proposed invention will help in securing data ensuring Patient Con-fidentiality, be compliant with respective local or regional regulations regarding Patient Data, Health Policies, Online Financial Transactions thus ensuring borderless access to healthcare, affordability by connecting to virtual network of doctors, providers and caregivers.

The proposed techniques enable online transfer of output data over a network, such as an intranet or internet. The following technique, in a web-redirection embodiment, includes receiving a generic data transfer request (e.g from a patient who has the proposed device at home, in-clinic or a remote place) from a website, or a mobile application to analyze the output data by a physician or a specialist who is based in a hospital or tertiary care setting or virtually connected to a network where the patient can access the physician for an expert advice of his clinical condition. Along with the patient data—the end user (patient, physician or nurse) can request for a type of payment to be initiated, processed and completed through the same device.

I claim:

1. An electronic stethoscope system comprising:
   a) a chest piece comprising a diaphragm, a bell, a micro-electro-mechanical (MEMS) microphone, an electronic amplifier, and a plurality of vibration transducers and acoustic transducers forming a 3-dimensional array, the chest piece is configured to:
      detect contact of the chest piece with an upper torso region of a human subject using one or more touch-based sensors integrated into the chest piece to dynamically trigger capturing of chest sounds and bodily vibrations of the human subject;
      capture sound signals corresponding to the chest sounds and vibration signals corresponding to the bodily vibrations via a sound capture component associated with the chest piece;
transduce the sound signals and the vibration signals into electrical signals via a microphone array within the chest piece, wherein the microphone array com-prises a set of vibration transducers and acoustic transducers, wherein the vibration transducers con-vert the vibration signals into acoustic signals, and wherein the electrical signals are amplified via an electronic amplifier communicatively connected to the microphone array to generate amplified electrical signals; and
perform signal pre-processing of the amplified electri-cal signals via a digital signal processing (DSP) unit within a processing unit, wherein the signal prepro-cessing comprises at least one of a noise filtration, beamforming, noise cancellation, a signal normal-ization, and conversion of the amplified electrical signals into electronic signal waveforms;
   b) the processing unit communicatively coupled to the chest piece, comprising:
      a data interpretation module to:
         analyze the electronic signal waveforms received from the DSP unit, by comparing the electronic signal waveforms with pre-defined waveforms based on standardized data;
         classify, using one or more artificial intelligence (AI) and machine learning (ML) classification models within the data interpretation module, one or more cardiac conditions comprising at least one of an aortic stenosis, a mitral regurgitation, and normal heart sounds, using pre-validated clinical datasets, wherein the classification comprises:
            analyzing input signal features corresponding to the electronic signal waveforms, the input sig-nal features comprising wavelet transforms, time-domain, frequency-domain, and time-fre-quency features for clinical relevance;
            determining at least one of the normal heart sounds and abnormal heart sounds based on at least one of the wavelet features and frequency band ranges in the electronic signal waveforms, wherein the AI and ML classification models comprise an Artificial Neural Network (ANN) based classification model configured to per-form clinical diagnostic decision-making using the input signal features, wherein determining at least one of the normal heart sounds and the abnormal heart sounds comprises:
               analyzing the input signal features to classify the input signal features as at least one of a normal pattern, an abnormal pattern, and a specific clinical condition-based pattern, wherein the ANN based classification model uses discrete wavelet transform, fuzzy logic, and fast Fourier transform (FFT) techniques to differentiate patterns in the input signal fea-tures;
               classifying at least one of the normal heart sounds and the abnormal heart sounds, using supervised machine learning techniques com-prising a support vector machine (SVM)-based classification model, based on the at least one of the wavelet features and the frequency band ranges in the signal waveforms, for the wavelet transforms features and the frequency-domain features in the input signal features;

analyzing one or more heart sounds comprising at least one of time features and frequency features extracted by linear decomposition and tiling partition of the time-frequency plane, time interval durations between systole and diastole, and frequency-based features and patterns with logistic regression and Gaussian distribution-based probabilities, via a hybrid classification model combining supervised learning and a hidden Markov model (HMM) for the time-frequency features;

classifying the one or more heart sounds as the normal heart sound or abnormal heart sound based on the analyzed one or more heart sounds comprising at least one of time features and frequency features, time interval durations between systole and diastole, and frequency-based features and patterns, using an unsupervised clustering-based classification model comprising k-Nearest Neighbors (kNN), based on the extracted time features and the frequency features by linear decomposition and tiling partition of the time-frequency plane; and classifying clinical diagnostic data using convolutional neural networks (CNNs) for two-dimensional (2D) time-frequency graphs and analyzing a time-domain signal using a deep learning framework comprising Recurrent Neural Networks (RNNs) and Long Short-Term Memory (LSTM) models for time-domain features; and generating at least one of one or more electronic wave forms and time parameters, frequency parameters and time-frequency parameters, based on determining the normal heart sounds, the abnormal heart sounds, and differentiated and classified the normal heart sounds, and the abnormal heart sounds, wherein the generated at least one of one or more electronic wave forms and time parameters, frequency parameters and time-frequency parameters is used to train the one or more AI and ML classification models; and an integrated diagnostic module to determine a diagnosis corresponding to the one or more cardiac conditions using the trained one or more AI and ML classification models, by comparing the electronic signal waveforms with information from electronic medical recordkeeping (EMR); and c) an output unit communicatively coupled to the processing unit configured to:

output at least one of a visual diagnostic output and a textual diagnostic output corresponding to the diagnosis based on the generated at least one of one or more electronic wave forms and time parameters, frequency parameters and time-frequency parameters, via at least one of a display, a display device, one or more cloud servers and one or more remote facilities, wherein the at least one of a visual diagnostic output and a textual diagnostic output comprises at least one of textual indication, waveforms, acoustics, augmented reality, virtual reality and mixed reality.

2. The electronic stethoscope system of claim 1, wherein the noise cancellation comprises filtering unwanted sound waves from at least one of the bell and the diaphragm moving across the skin, hair, or clothing of the human subject, and reducing ambient noise.

3. The electronic stethoscope system of claim 1, further comprising an additional microphone to record the voice of a user with voice-to-text conversion, for Electronic Medical Recordkeeping (EMR).

4. The electronic stethoscope system of claim 1, further comprising a payment gateway interface for transactions and virtual services.

* * * * *